US012752041B2

(12) United States Patent
Humayun et al.

(10) Patent No.: US 12,752,041 B2
(45) Date of Patent: Oct. 6, 2026

(54) POLYMERIC PATCH SCAFFOLDS FOR ARTICULAR CARTILAGE REGENERATION

(71) Applicants: UNIVERSITY OF SOUTHERN CALIFORNIA, Los Angeles, CA (US); CALIFORNIA INSTITUTE OF TECHNOLOGY, Pasadena, CA (US)

(72) Inventors: Mark S. Humayun, Glendale, CA (US); Carlos Eduardo da Silveira Franciozi, Los Angeles, CA (US); Tzu-Chieh Chou, Pasadena, CA (US); Yu-Chong Tai, Pasadena, CA (US); Damien C. Rodger, Glendale, CA (US); C. Thomas Vangsness, Jr., Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 16/377,979

(22) Filed: Apr. 8, 2019

(65) Prior Publication Data

US 2019/0307928 A1 Oct. 10, 2019

Related U.S. Application Data

(60) Provisional application No. 62/654,249, filed on Apr. 6, 2018.

(51) Int. Cl.
*A61L 31/16* (2006.01)
*A61B 17/11* (2006.01)
(Continued)

(52) U.S. Cl.
CPC ............ *A61L 31/16* (2013.01); *A61F 2/0063* (2013.01); *A61K 35/28* (2013.01);
(Continued)

(58) Field of Classification Search
CPC ...... A61L 31/16; A61L 27/3834; A61L 27/54; A61L 2430/06; A61L 2430/10; A61F 2/0063; A61F 2002/30766; A61K 35/28
See application file for complete search history.

(56) References Cited

U.S. PATENT DOCUMENTS

2002/0110544 A1* 8/2002 Goldberg ............. C12N 5/0663 435/325
2007/0148206 A1* 6/2007 Demirel ................... B05D 1/60 427/2.24
(Continued)

FOREIGN PATENT DOCUMENTS

WO WO-2015051042 A2 * 4/2015 ............. A61L 27/38
WO WO-2018031491 A1 * 2/2018 ......... A61F 2/30942

OTHER PUBLICATIONS

Da Silveira Franciozi et al., "Parylene scaffold for cartilage lesion", Biomed Microdevices, Apr. 8, 2017, 19:26, pp. 1-11. (Year: 2017).*
Definition of "sheet". Accessed online on May 20, 2023 at <https://www.merriam-webster.com/dictionary/sheet>. (Year: 2023).*
(Continued)

*Primary Examiner* — Sue X Liu
*Assistant Examiner* — Casey S Hagopian
(74) *Attorney, Agent, or Firm* — Mark P. Mathison

(57) ABSTRACT

A polymeric substrate for treating a chondral or osteochondral defect includes a polymeric sheet having a predetermined shape and size for placement over a chondral or osteochondral defect. The polymeric sheet defines suture openings therein that allow fixation of the polymeric scaffold. Characteristically, the polymeric sheet includes biocompatible polymer. A method for treating a subject having a chondral or osteochondral defect is also provided.

25 Claims, 12 Drawing Sheets

(51) Int. Cl.

| | |
|---|---|
| ***A61F 2/00*** | (2006.01) |
| ***A61F 2/30*** | (2006.01) |
| ***A61K 35/28*** | (2015.01) |
| ***A61L 27/38*** | (2006.01) |
| ***A61L 27/54*** | (2006.01) |
| ***A61L 31/08*** | (2006.01) |
| ***A61L 31/14*** | (2006.01) |
| ***A61P 19/04*** | (2006.01) |

(52) U.S. Cl.
CPC ........... *A61L 27/3834* (2013.01); *A61L 27/54* (2013.01); *A61L 31/08* (2013.01); *A61L 31/148* (2013.01); *A61P 19/04* (2018.01); *A61B 17/1146* (2013.01); *A61F 2002/30766* (2013.01); *A61L 2430/06* (2013.01); *A61L 2430/10* (2013.01)

(56) References Cited

U.S. PATENT DOCUMENTS

2010/0168864 A1* 7/2010 White .................. A61B 17/562
623/18.11
2012/0177702 A1* 7/2012 Altschuler .............. A61L 27/34
423/430
2018/0021138 A1* 1/2018 Estes ................... A61F 2/30756
623/16.11

OTHER PUBLICATIONS

Humphrey, "Using Parylene for Medical Substrate Coating", Medical Plastics and Biomaterials Magazine, Jan. 1996, pp. 1-7. (Year: 1996).*

Lu, B. et al., "Mesh-supported submicron parylene-C membranes for culturing retinal pigment epithelial cells," Biomed Microdevices (2012) 14, pp. 659-667.

* cited by examiner 6 weeks 6 weeks 9 weeks 9 weeks 12 weeks 12 weeks

POLYMERIC PATCH SCAFFOLDS FOR ARTICULAR CARTILAGE REGENERATION

CROSS REFERENCE

This application claims the benefit of U.S. provisional application Ser. No. 62/654,249 filed Apr. 6, 2018, the disclosure of which is incorporated in its entirety by reference herein.

TECHNICAL FIELD

In at least one aspect, the present invention is related to methods for treating cartilage defects and lesions; and in particular, the present invention is related to methods for treating cartilage defects and lesions that are augmented with a polymeric scaffold.

BACKGROUND

Articular cartilage is aneural, alymphatic and avascular. It is nourished by diffusion of nutrients derived from the synovial fluid. The microenvironment of the articular cartilage plays an important role in its biomechanical function. The properties of this tissue are related to the composition of its extracellular matrix, mainly composed of proteoglycans and hyaluronic acid entangled in a dense network of collagen fibers that retain large amounts of water. The structures of these molecules play major roles in determining the resilience of the tissue to tension and compression forces. Chondrocytes are the only cell type of the articular cartilage. They maintain tissue homeostasis, react to injury and carry out cartilage remodeling. However, this tissue is relatively hypocellular and the chondrocytes do not move through the matrix. Some of these characteristics are responsible for the poor healing response of this tissue.

Partial thickness articular cartilage defects do not heal spontaneously, while the healing process of full-thickness osteochondral lesions leads to a fibrous cartilage tissue of inferior biomechanical properties addressed as fibrocartilage (Mankin 1982; Franciozi et al. 2013; Poole et al. 2001; Hunziker and Rosenberg 1996; Shapiro et al. 1993; Pouran et al. 2016). Articular cartilage injury often results in pain, disability and in some cases, the development of joint degeneration and arthritis (Cicuttini et al. 2005; Ding et al. 2006; Franciozi et al. 2013). Cartilage lesions can be seen in 60% of all arthroscopies with 9% of those being full thickness lesions eligible for surgical treatment (Widuchowski et al. 2007). The incidence of knee arthroscopy was 99 per 100,000 person-year from 1997 to 2012 in Finland for traumatic meniscus lesions, and 91 per 100,000 persons-year from 2005 to 2007 in Denmark for anterior cruciate ligament lesions (ACL) for 15 to 39 year old patients (Mattila et al. 2016; Lind et al. 2009). If 10% of these patients exhibit a full thickness cartilage lesion eligible for surgical treatment, this clearly poses a common and important health management problem. Current surgical treatments for cartilage lesions include reparative and reconstructive procedures. Reparative procedures for knee cartilage injury include microfracture, abrasion arthroplasty, drilling, and biological procedures involving cell therapies and bioabsorbable scaffolds. Reconstructive procedures available for treating knee cartilage injuries are the osteochondral autograft transplantation, allograft transplantation, and the use of unabsorbable scaffolds (Gracitelli et al. 2016).

In addition, current studies have shown the use of a synthetic scaffold has reduced friction and protected the repair site in shoulder cuff repairs. In a study done by Ciampi et al. (Zumstein, M. A., et al., 2016), results show a significant decrease in re-tear rates when augmented with a polypropylene patch compared to repair-only controls. In addition, this study showed that when supplemented with a scaffold, there was an increase in abduction strength and elevation on follow up examinations. Another study examining functionality, the repairs using a patch showed increased functional improvements in the shoulder when tendons were reinforced (Proctor, Christopher S., 2014).

The attachment of a bio-inductive collagen implant to partial-thickness tears of the tendon showed clinical outcomes were improved significantly in a one year follow up scores with an increase in the mean tendon thickening of 2.0 mm, demonstrated in a study carried out by Schlegel et al (Schlegel, Theodore F., et al.). MRIs examined 12 months post-surgery showed evidence of completely healed defects or a considerable reduction in the size of the defect. No patients in this study had an increase in tears when following postoperative protocols or underwent revision surgery. When examined using MRIs, the tendons showed a layer of tissue growth over the bursal surface, contributing to the increase in significant tendon thickness in multiple patients. At one year follow ups, the new tissue growth had become indistinguishable from original tendon tissue. Examining pain and functionality scores, there was a significant improvement in one-year post-operative measurements. Pain scores improved significantly from baseline, ASES index scores improved from pre- to post-op at one-year (Schlegel, Theodore F., et al., 2018).

In a prospective study examining 61 large rotator cuff repairs (3 to 5 cm), surgical enhancement using porcine extra cellular matrix scaffolds showed significantly improved outcome scores of muscle strength, functionality, and range of motion at 12-month follow ups compared to preoperative scores (Lederman, Evan S., et al., 2016).

A supplemental scaffold during arthroscopic repair provides a mechanical advantage during healing and ideally prevents an increase in tendon re-tears (Gillespie, Robert J., et al., 2016). It has been shown that there is an advantage of strength in synthetic grafts compared to biological grafts as well as a decrease in disease transmission. A three-year cohort study examining a polypropylene graft versus traditional repair with no graft showed a significant increase in UCLA scores, mean elevation and abduction strength at 36 weeks post-op compared to controls. In addition to increased scores, the polypropylene patch also showed higher rates of durability measured by lower re-tear rates (Gillespie, Robert J., et al., 2016).

Recently, a bio-inductive implant has become available that offers mechanical assistance in rotator cuff repairs and prevent tear increases in partial or full thickness tears (Regeneten) (Smith & Nephew, 2019). The patch is a bovine Achilles tendon anchored to the tear site to reduce strain and aid new tendon growth. The patch will absorb 6 months after placement, being replaced with new tissue growth. In a prospective multi-center study of 31 patients, patch effectiveness was assessed using MRI at 3 and 12-month follow up. Results show an improved ASES pain score compared to baseline (Smith & Nephew, 2019).

The addition of biological factors such as the application of growth factors, cytokines, mesenchymal stem cells, and various scaffolds, as well as a combination of these, have been studied to improve healing at the site of rotator cuff tears (Zumstein, M. A., et al., 2016).

A cocktail of growth factors within a collagen type I sponge implanted in vitro into a rotator cuff tear site showed an accelerated healing response compared to controls as well as an increase in bone and soft tissue volume 6 and 12 weeks after implantation compared to controls (Zumstein, M. A., et al., 2016).

Studies examining the collection and application of bone marrow aspirate concentrate (BMAC) to the tear site may show improved healing. Current literature is limited, however, promising. A study of 14 patients with complete tears were treated surgically with autologous bone marrow stem cells injected into tear sites (Hernigou, Philippe, et al., 2014; Gomes, Joao L. Ellera, et al., 2011). In a 12 month follow up, MRIs showed the integrity of the tendon visible in all subjects (Hernigou, Philippe, et al., 2014; Gomes, Joao L. Ellera, et al., 2011). To obtain bone marrow MSCs, cells are harvested arthroscopically from the humeral head during reconstruction. These cells were then differentiated successfully into connective tissue progenitor cells (Mazzocca, Augustus D., et al., 2010). Another way MSCs have been obtained and differentiated, is through harvest from the humerus and treated with insulin (Mazzocca, Augustus D., et al., 2011). Cells treated this way were shown to have tendon characteristics (Zumstein, M. A., et al., 2016; Mazzocca, Augustus D., et al., 2011).

A 2014 study by Hernigou, rotator cuff reconstructions using applied MSCs showed decreased re-tearing compared to controls (Zumstein, M. A., et al., 2016; Hernigou, Philippe, et al., 2014). 45 patients were administered bone-marrow derived MSCs during arthroscopic repair and compared to 45 control patients who underwent standard surgical repair without MSCs. Patients were assessed at three and six months, 1 year and two year follow ups using MRIs. Results showed the group who received bone marrow derived MSCs had an accelerated rate of healing compared to controls, with 100% of the experimental group healed at 6-months compared to only 30 control patients. It was determined that at the 10 year follow up, those who received stem cell injections had lower rates of repeated tears compared to controls (Hernigou, Philippe, et al., 2014).

The evaluation of arthroscopic patch application supplemented with bone marrow stimulation in rotator cuff repairs of 21 patients showed a significantly lower re-tear rate and medial-row failure rates compared to 54 control patients who underwent standard arthroscopic repair (Yoon, Jong Pil, et al., 2016). The combination of a biological supplement with a scaffold applied to the site of injury provides a biological stimulation of repair as well as a mechanical advantage to healing rates determined by a significantly improved difference in re-tear rates between groups (Yoon, Jong Pil, et al., 2016).

Despite this myriad of treatments, these techniques are unsatisfactory due to poor quality of the repaired cartilage, morbidity, cost, availability, long-term outcomes and survivorship. Moreover, no current human studies examine combination uses of scaffolds with MSCs or growth factors, but animal models have shown promising results (Gillespie, Robert J., et al., 2016).

Accordingly, improved methods for treating cartilaginous defects and lesions are needed.

SUMMARY

The present invention solves one or more problems of the prior art by providing in at least one aspect a polymeric scaffold for treating a chondral defect, an osteochondral defect, a rotator tendon defect, a rotator cuff tear, or another region needing tendon regeneration. The polymeric scaffold includes a polymeric sheet having a predetermined shape and size for placement over the chondral defect or the osteochondral defect or the rotator tendon defect or the rotator cuff tear or the region needing tendon regeneration. The placement is for tendon repair or regeneration. The polymeric sheet defines suture openings therein that allow fixation of the polymeric scaffold. Characteristically, the polymeric sheet includes a biocompatible polymer.

In another aspect, a method for treating a subject having a chondral defect, an osteochondral defect, rotator tendon defect, a rotator cuff tear or some other region needing tendon regeneration, is provided. The method includes a step of identifying a subject having the chondral defect, the osteochondral defect, the rotator tendon defect, the rotator cuff tear, or the region needing tendon regeneration. The scaffold set forth herein is placed over the chondral defect, the osteochondral defect, the rotator tendon defect, the rotator cuff tear, or the region needing tendon regeneration and then fixed thereto with sutures.

DETAILED DESCRIPTION

Figure 1A:
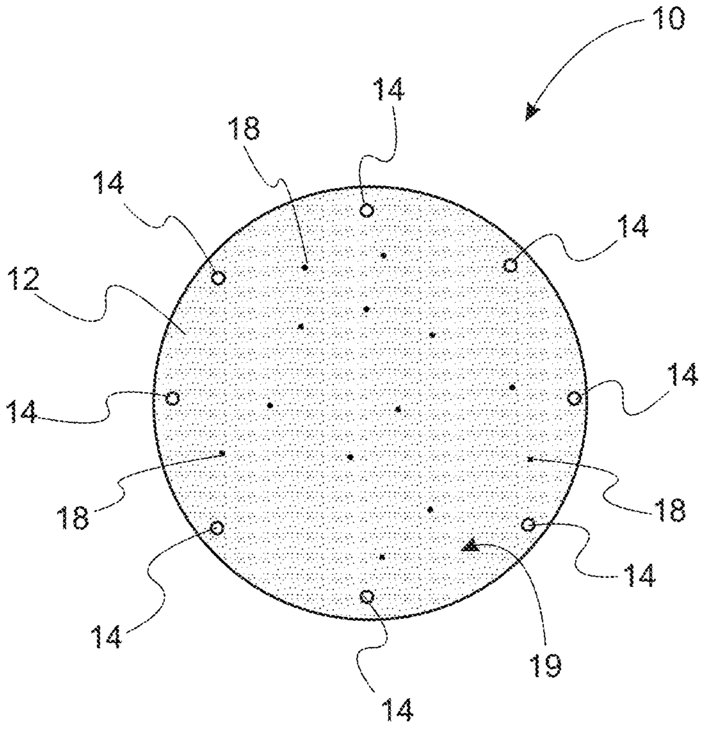
FIG. 1A: Schematic illustration of a polymeric scaffold.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

Abbreviations:

"ICRS" means International Cartilage Repair Society.

"MSC" means mesenchymal stem cells.

The term "parylene" refers to chemical vapor deposited poly(p-xylylene) polymers, and in particular, chemical vapor deposited poly(p-xylylene) polymers. Parylenes can be unsubstituted or include various substituents on the xylelene group. Examples of suitable substituents include, but are not limited to, halo (e.g., chloro and fluoro), $C_{1-6}$ alkyl (e.g., methyl, ethyl), methylene amine groups, and the like.

The term "parylene C" means (poly[chloro-p-xylylene]).

The term "parylene D" means (poly[dichloro-p-xylylene]).

The term "parylene M" means poly(methyl-p-xylylene).

The term "parylene E" means poly(ethyl-p-xylylene).

The term "parylene N" means poly(para-xylylene).

The term "parylene HT" refers to poly(p-xylylene) with hydrogen substituted with fluorine.

The term "parylene A" refers to poly(p-xylylene) with one amine group per p-xylylene unit.

The term "parylene AM" refers to poly(p-xylylene) with one methylene amine group per p-xylylene unit.

The term "biocompatible material" means a material that is non-immunogenic, non-allergenic and causes minimal undesired physiological reactions.

The term "biocompatible polymer" means a polymer that is non-immunogenic, non-allergenic and causes minimal undesired physiological reactions.

In general, a biocompatible scaffold for treating a chondral defect or an osteochondral defect or a rotator tendon defect or a rotator cuff tear or another region needing tendon regeneration is provided. The biocompatible scaffold includes a sheet having a predetermined shape and size for placement over a chondral or osteochondral or tendon defect. Advantageously, the sheet defines openings therein that allow fixation of the scaffold. In particular, suture holes allow suturing of biocompatible scaffold to surrounding cartilage proximate to the chondral defect or the osteochondral defect or the rotator tendon defect or the rotator cuff tear or the region needing tendon regeneration being treated. In some instance, the biocompatible scaffold can also be used for tendon regeneration. Advantageously, the sheet includes and/or is a biocompatible material and in particular, a biocompatible polymer as set forth below.

With reference to FIG. 1A, a polymeric scaffold (e.g., a polymeric membrane) for treating a chondral defect or an osteochondral defect or a rotator tendon defect or a rotator cuff tear or another region needing tendon regeneration is schematically illustrated. Polymeric scaffold 10 includes polymeric sheet 12 having a predetermined shape and size for placement over a chondral or osteochondral defect. Polymeric sheet 12 defines suture holes 14 therein that allow fixation of the polymeric scaffold. In particular, suture holes 14 allow suturing of polymeric scaffold 10 to surrounding cartilage proximate to the chondral defect or the osteochondral defect or the rotator tendon defect or the rotator cuff tear or the region needing tendon regeneration being treated. In some instances, the polymeric scaffold can also be used for tendon regeneration.

In a variation, polymeric sheet 12 (or in general the sheet of the biocompatible scaffold) further defines micropores 18 that allow nutrients and macromolecules diffusion therethrough when the polymeric scaffold is placed in a subject being treated for a chondral defect or an osteochondral defect or a rotator tendon defect or a rotator cuff tear or another region needing tendon regeneration. In this context, such defects include lesions thereof such as osteoarthritis, rotator cuff tears, and the like. Such micropores can have an average diameter from about 10 nm to about 5 microns. In a refinement, the micropore have an average diameter from about 30 nm to about 1 microns.

In another variation, polymeric sheet 12 (or in general the sheet of the biocompatible scaffold) further includes one or more biological factors embedded in and/or adsorbed on the polymeric sheet that improve healing of a defect. Examples of such biological factors include, but are not limited to, growth factors, cytokines, mesenchymal stem cells, and combinations thereof. In particular, mesenchymal stem cells embedded in and/or adsorbed on polymeric sheet 12 can be particularly useful. In a refinement, polymeric sheet 12 has at least one cell adhesion factor embedded in and/or adsorbed thereon. Examples of such cell adhesion factors include, but are not limited to factor selected from the group consisting of fibronectin, laminin, collagen, vitronectin and tenascin, and combinations thereof.

Polymeric scaffold 10 includes polymeric sheet 12 (or in general the sheet of the biocompatible scaffold) having a predetermined shape and size for placement over a chondral defect or an osteochondral defect or a rotator tendon defect or a rotator cuff tear or another region needing tendon regeneration. The polymeric scaffold of FIG. 1A depicts a device for treating a 4 mm circular lesion. However, it should be appreciated that the polymeric scaffold is not limited to any particular shape, size, or thickness. In general, polymeric scaffold 10 is micromachined into a shape matching outlines of the cartilage defect or lesion being treated. In a refinement, polymeric scaffold 10 is slightly larger than the cartilage defect or lesion being treated (e.g., having an area from 1 to 20 percent larger than the lesion or defect). In a refinement, face 19 of the polymeric sheet has an area from about 10 $mm^2$ to 100 $cm^2$. Although the present embodiment is not limited by the thickness of polymeric sheet 12, the thickness should be sufficient to maintain the structural integrity of polymeric scaffold 10. In this regard, useful a thickness is at least 100 microns (e.g., from about 100 microns to about 1 mm).

The biocompatible polymer that forms polymeric sheet 12 can be biostable, bioabsorbable, biodegradable or bioerodible. In this context, the terms biodegradable, bioabsorbable, and bioerodible are used interchangeably. Biodegradable, bioabsorbable, and bioerodible polymer are polymer that can be completely degraded and/or eroded when exposed to bodily fluids. Moreover, these polymer can be gradually resorbed, absorbed, and/or eliminated by the body. Biostable refers to polymers that are not biodegradable. The biocompatible polymers can be non-synthetic (i.e., naturally-occurring or naturally-derived) or synthetic. Examples of non-synthetic biodegradable polymers include but are not limited to proteins (e.g., collagen), polysaccharides, biopolyesters (e.g., polyhydroxybutyrate, polylactic acid). Examples of synthetic biodegradable polymers include, but are not limited to, poly(amides), poly(peptides); poly(esters), poly(anhydrides), poly(orthoesters), poly(carbonates), and chemical derivatives thereof, and copolymers thereof, and combinations thereof. Examples of biostable polymers include, but are not limited to, silicones, poly(ethers) (e.g., poly(ethylene oxide)), poly(ethylene glycol), and poly(tetramethylene oxide)), vinyl polymers—poly(acrylates) and poly(methacrylates), poly(vinyl alcohol), poly(vinyl pyrolidone), poly (vinyl acetate), poly(urethanes), cellulose, poly(siloxanes), and any chemical derivatives thereof, and copolymers thereof, and combinations thereof.

In a variation, polymeric sheet 12 is formed from a substituted or unsubstituted parylene. In this variation, polymeric scaffold 10 is a parylene scaffold. Examples of useful parylenes include, but are not limited to, parylene C, parylene D, parylene N, parylene HT, parylene A, parylene AM, and combinations thereof. Advantageously, the parylene patch scaffold 10 can be used to treat osteoarthritis, cartilage lesions and osteochondral lesions thereby allowing articular cartilage regeneration. Parylene C is found to be particularly useful for forming the parylene scaffold. Parylene-C is a USP class VI, ISO 10993 biocompatible polymer, approved for chronic implantation in the human body and demonstrates ideal mechanical strength, biostability, barrier, and chemical inertness properties (Rodger et al. 2008). It has been successfully utilized in biomedical microdevices and is currently being tested in a clinical trial as a scaffold for pigment retinal epithelial stem cells for macular degeneration (Diniz et al. 2013; Lu et al. 2012). However, prior to the present invention, parylene-C has never been tested as a cartilage scaffold.

Figure 1B:
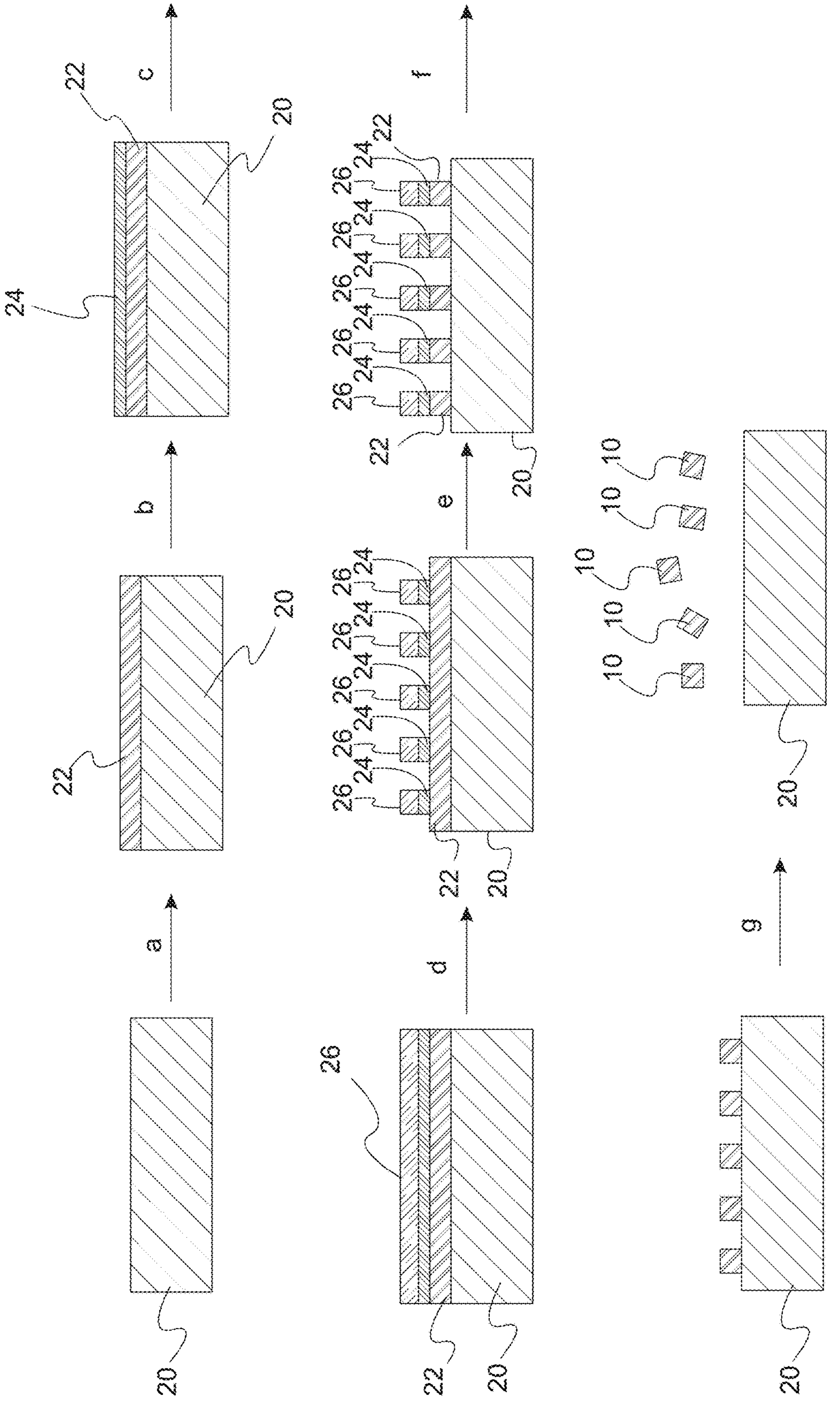
FIG. 1B: Schematic flowchart of a method for forming the polymeric scaffold of FIG. 1A.

With reference to FIG. 1B, a schematic flowchart illustrating the preparation of a parylene scaffold of FIG. 1A is provided. In step a), substrate 20 (e.g., a silicon wafer) is coated with parylene layer 22 by chemical vapor deposition. Examples of parylenes are set forth above. In step b), metal layer 24 (e.g., 300 nm thick aluminum) is deposited onto parylene layer 22. In step c), a patterned photoresist layer 26 is coated onto metal layer 24. In step d), exposed regions of metal layer 24 are etched to form a mask for parylene layer 22. In step e), parylene layer 22 is subjected to oxygen plasma etching to form parylene scaffolds 30 of FIG. 1A. Finally, parylene scaffolds 30 are released from substrate 20 in a water bath.

Figure 2A:
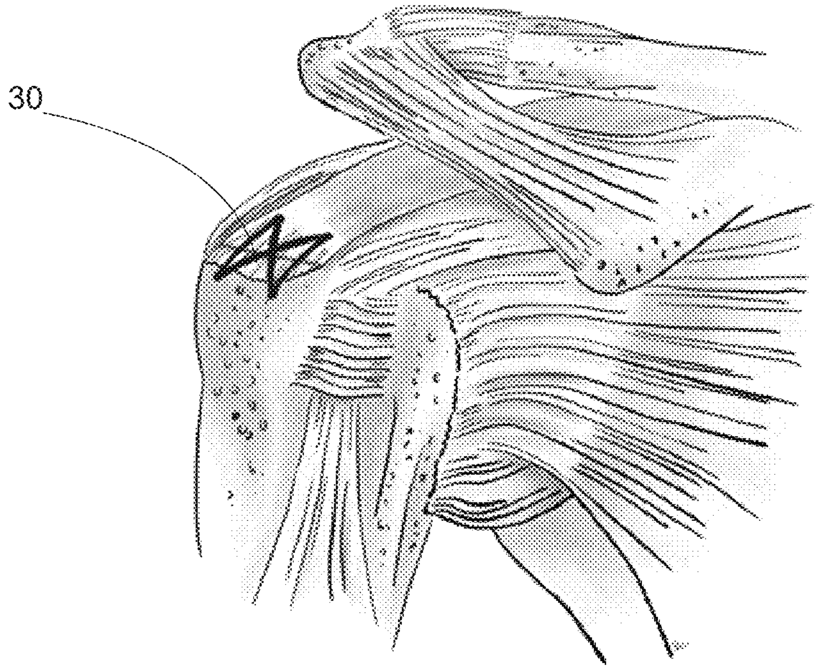
FIG. 2A. Illustration of rotator cuff repair without augmentation.
Figure 2B:
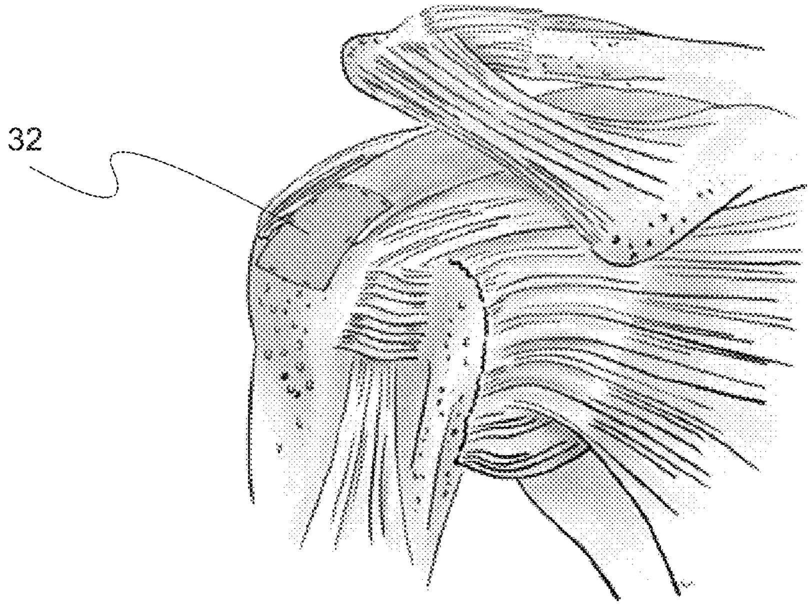
FIG. 2B. Illustration of rotator cuff repair covered with polymeric patch embedded with MSCs
Figures 3A, 3B, 3C, 3D, 3E, 3F, 3G, 3H, 3I, 3J, 3K, 3L:
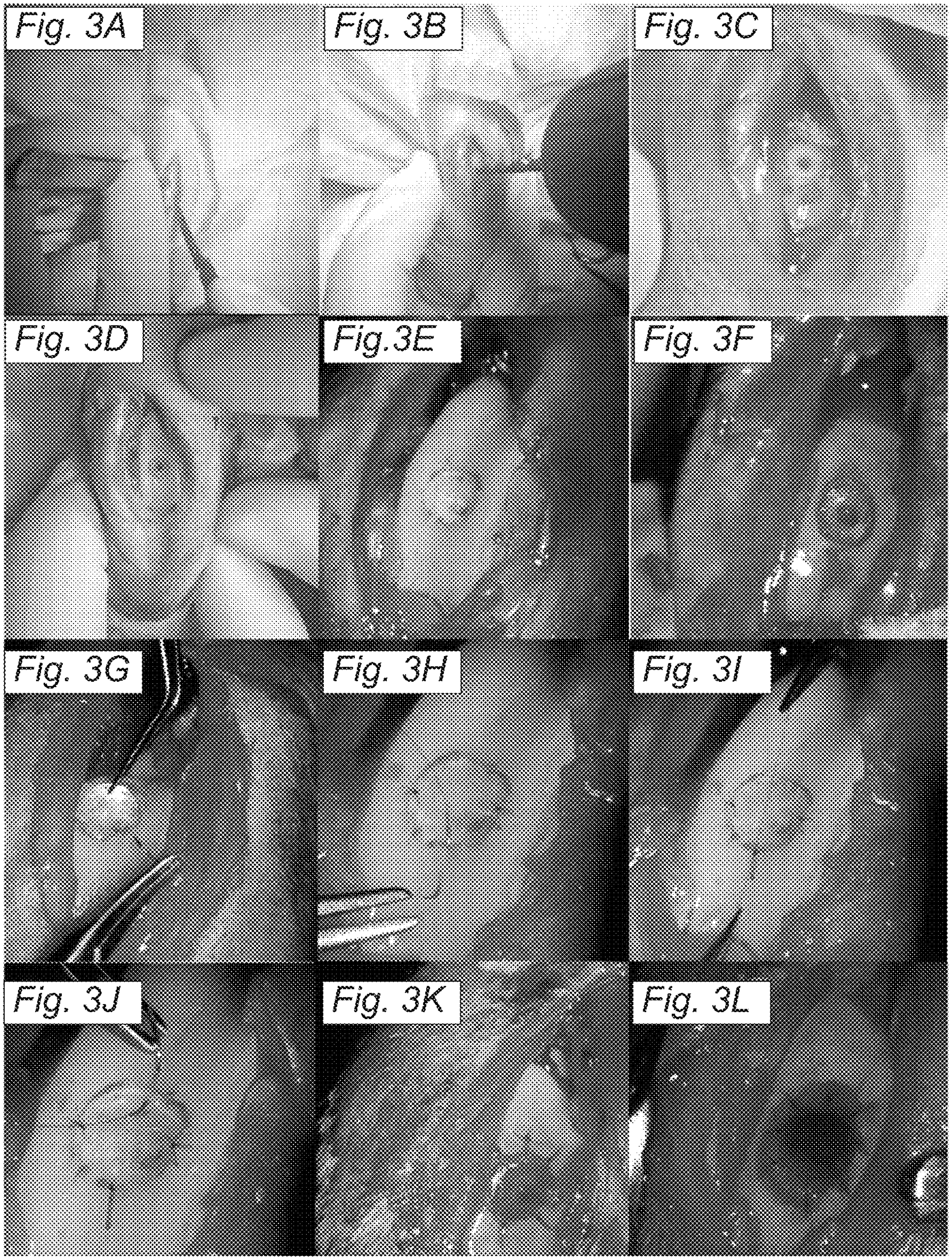
FIGS. 3A, 3B, 3C, 3D, 3E, 3F, 3G, 3H, 3I, 3J, 3K, and 3L: Surgery, osteochondral defect model and parylene scaffold implantation. A. Medial parapatellar incision at the extensor mechanism and knee capsule. B. Patella is retracted laterally exposing the trochlea and an osteochondral defect is made at the trochlear groove using a 4 mm diameter brad point drill bit to the depth of 2 mm. C. Osteochondral defect with debris. D. Osteochondral defect after washing with saline solution. E. Detailed image of the osteochondral defect depicting the 4 mm×2 mm lesion and the central microfracture hole 2 mm deeper. F. The osteochondral defect and the central microfracture hole allow blood derived from the bone marrow to fill the defect forming a clot. G. Parylene scaffold microsurgical implantation using a microscope. H. 10-0 nylon suture passage through the prefabricated peripheral 200 μm hole on the scaffold anchoring it to the cartilage just above the subchondral bone. I. 10-0 nylon suture knot tightening securing the scaffold to the surrounding cartilage. J. The first four sutures are made on the four cardinal points to determine position. K. Parylene scaffold anchored to the surrounding cartilage through the eight peripheral holes with underlying bleeding coming from the central microfracture hole and the osteochondral defect. L. Final view showing the parylene scaffold acting as a lid, which stabilizes the blood clot containing the bone marrow mesenchymal stem cells and helps the derived immature repair tissue withstand the patellofemoral shearing forces.

In another embodiment, a method for treating a subject having a chondral defect or an osteochondral defect or a rotator tendon defect or a rotator cuff tear or a region needing tendon regeneration or combinations thereof is provided. The method includes a step of identifying a subject having a chondral defect or an osteochondral defect or rotator tendon defect or a rotator cuff tear or a region needing tendon regeneration. The identification of such defects can include various imaging techniques (e.g., x-ray, MRI, etc.), arthroscopy, physical examination, and the like. The polymeric scaffold (or in general the biocompatible scaffold) set forth above is placed over the chondral defect or the osteochondral defect or the rotator tendon defect or the rotator cuff tear or the region needing tendon regeneration and fixed thereto with sutures. In a refinement, the chondral defect or the osteochondral defect or the rotator tendon defect or the rotator cuff tear or the region needing tendon regeneration is surgically repaired prior to placement of the polymeric scaffold (e.g., suturing of a tear). FIG. 2A illustrates conventional repair of a rotator cuff tear not using a polymeric scaffold. FIG. 2A show a tear sutured together with sutures 30 without a polymeric scaffold being applied. FIG. 2B illustrates rotator cuff in which polymeric scaffold 32 having embedded MSCs embedded in and/or adsorbed on the polymeric sheet is applied over the sutures.

The following examples illustrate the various embodiments of the present invention. Those skilled in the art will recognize many variations that are within the spirit of the present invention and scope of the claims.

1. Summary

Parylene scaffold feasibility in cartilage lesion treatment was evaluated as a novel paradigm combining a reparative and superficial reconstructive procedure. Fifteen rabbits were used. All animals had both knees operated and the same osteochondral lesion model was created bilaterally. The parylene scaffold was implanted in the right knee, and the left knee of the same animal was used as control. The animals were euthanized at different time points after surgery: four animals at three weeks, three animals at six weeks, four animals at nine weeks, and four animals at 12 weeks. Specimens were analyzed by International Cartilage Repair Society (ICRS) macroscopic evaluation, modified Pineda histologic evaluation of cartilage repair, and collagen II immunostaining. Parylene knees were compared to its matched contra-lateral control knees of the same animal using the Wilcoxon matched-pairs signed rank. ICRS mean±SD values for parylene versus control, three, six, nine and twelve weeks, respectively: 7.83±1.85 versus 4.42±1.08, p=0.0005; 10.17±1.17 versus 6.83±1.17, p=0.03; 10.89±0.60 versus 7.33±2.18, p=0.007; 10.67±0.78 versus 7.83±3.40, p=0.03. Modified Pineda mean±SD values for parylene versus control, six, nine and twelve weeks, respectively: 3.37±0.87 versus 6.94±1.7, p<0.0001; 5.73±2.05 versus 6.41±1.7, p=0.007; 3.06±1.61 versus 6.52±1.51, p<0.0001. No inflammation was seen. Parylene implanted knees demonstrated higher collagen II expression via immunostaining in comparison to the control knees. Parylene scaffolds are a feasible option for cartilage lesion treatment and the combination of a reparative to a superficial reconstructive procedure using parylene scaffolds led to better results than the reparative procedure alone.

2 Materials and Methods

2.1 Parylene Membrane Fabrication and Sterilization

A parylene-C scaffold was fabricated with 9 μm thickness, 4 mm diameter, with eight peripheral 200 μm diameter holes intended for suture passage (FIGS. 1A and 1B). The scaffold was sterilized by 100% ethylene oxide using a 3 M Steri-Vac Sterilizer/Aerator Model 5XL (3 M, Ontario, Canada).

2.2 Animals and Groups

All animal studies were approved by the University of Southern California Institutional Animal Care and Use Committee and conformed to the Animal Research: Reporting In Vivo Experiments (ARRIVE) guidelines (Franciozi et al. 2013). Fifteen mature male New Zealand White Rabbits were used. The rabbits were 6 months old and weighed approximately 3.5 kg each. The animals were housed with appropriate bedding and provided free access to water and food. They were kept in standard single cages under controlled temperature and light conditions. All animals had both knees operated and the same osteochondral lesion model was created bilaterally. The parylene scaffold was implanted in the right knee, and the left knee of the same animal was used as control. The animals were euthanized at different time points after parylene implantation: four animals at three weeks after surgery, three animals at six weeks after surgery, four animals at nine weeks after surgery, and four animals at 12 weeks after surgery.

2.3 Surgery

2.3.1 Surgery Preparation

The rabbits were pre-anesthetized by an intramuscular injection of 13.3 mg/kg xylazine and 50 mg/kg ketamine. Gas anesthesia was utilized placing a face mask tightly over the rabbit's face. Isoflurane was used at 2.5% in oxygen (1 l/min) to maintain anesthesia. At the anesthesic induction, 3 mg/kg intramuscular gentamycin was administered as antibiotic prophylaxis. To protect the corneas from drying, a bland ophthalmic ointment was applied to each eye. After anesthesia, the knee joints were shaven. The animal was moved to the aseptic surgical space, after a sterile drape was placed over the table. The rabbit was placed in supine position and prepared for the aseptic surgical procedure. The site was cleansed and disinfected with iodine and alcohol. The scrub was alternated between iodine and alcohol and it was repeated three times. The surgeon used a surgical mask, cap, and sterile surgical gloves. The sterile packs, including the sterile barrier, instruments and equipment were opened. A sterile drape with a hole for each knee covered the animal and iodine was applied and permitted to dry in place.

2.3.2 Surgery and Osteochondrol Defect Model

A no. 15 surgical scalpel blade was used to make an anteromedial incision 2.5 cm long to open the skin and subcutaneous tissue. The same blade was used to make a 3 cm medial parapatellar incision in the extensor mechanism and knee capsule. After gaining access to the knee joint, the patella was retracted laterally and the trochlea was exposed. An osteochondral defect was made at the interchondylar groove of each femur (trochlear groove) using a 4 mm diameter brad point drill bit to a depth of 2 mm. The brad point drill bit prevented slippage once introduced at the desired trochlear site. As cartilage thickness is just 0.44±0.08 mm at the rabbit trochlear groove, by drilling to 2 mm depth, the defect penetrates the subchondral bone causing some bleeding and the formation of repair tissue. Also, the central hole made by the tip of the brad point drill penetrates another 2 mm more (total of 4 mm depth for the tip) acting as a microfracture hole. The defect was washed of any remaining debris with saline solution. The osteochondral defect and the central microfracture hole allowed blood derived from the bone marrow to fill the defect forming a clot. This osteochondral defect acted as a lesion while at the same time starting reparative bone marrow stimulation by subchondral bone bleeding. In this healing process, bone marrow mesenchymal stromal cells migrate into the blood clot and form fibrocartilage, which is biomechanically inferior to articular cartilage and more prone to degeneration over the long term (Gracitelli et al. 2016; Chu et al. 2010) (FIGS. 3A-F). A parylene scaffold was implanted over the right knee lesion as detailed below. No other treatment procedure was performed in the left knee, which acted as a control. The articular capsule and the skin were closed with 4-0 Vicryl suture (Ethicon, Johnson & Johnson, Somerville, New Jersey), the rabbits returned to their cages after anesthesia recovery and were allowed free cage activity with free access to water and food. The animals were monitored with regards to mobility and eating/drinking habits to ensure their health after the surgery. Postoperative analgesia was provided with either buprenorphine (0.01-0.05 mg/kg) administered subcutaneously every 12 h for at least 48 h post-operatively or buprenorphine SR (0.06-0.3 mg/kg) administered subcutaneously once a day for at least 48 h post-operatively. Meloxican 0.2-0.6 mg/kg SC or PO was given every 24 h as necessary up to 5 days post-operatively. 2.3.3 Parylene scaffold implantation After the aforementioned osteochondral defect was fashioned, the parylene scaffold was implanted in the right knee. The implantation was performed using a microscope with zoom and focus controlled by a foot pedal (Zeiss Opmi MDO/S5 Microscope, Colorado, USA) and 10-0 Nylon suture (Ethicon, Johnson & Johnson, Somerville, New Jersey). The peripheral 200 μm holes on the scaffold were used to pass the suture and fix it to the surrounding cartilage border at eight different sites. Microsurgical techniques and 10-0 nylon sutures were necessary because the mean cartilage thickness at the rabbit trochlear groove is just 0.44±0.08 mm (Chu et al. 2010). Larger sutures cheese-wired through the cartilage. The scaffold was fixed at the defect, the patella was reduced, the knee was subjected to 30 flexion-extension movements along the range of motion, the patella was retracted laterally again and the scaffold was examined regarding its fixation (FIGS. 3G-L). 2.3.4 Euthanasia The animals were euthanized at different time points after scaffold implantation: four animals at three weeks after surgery, three animals at six weeks after surgery, four animals at nine weeks after surgery, and four animals at 12 weeks after surgery. Euthanasia was carried out by an intracardiac injection of pentobarbital (100 mg/kg) under general anesthesia as described in Section 2.3.1.

2.4 Macroscopic Evaluation

Macroscopic evaluation was performed by taking photographs on the same day the animal was euthanized. The resected distal femur was stripped of soft tissue. Each knee was photographed alone and with its contra-lateral side matched pair. A video was also made recording each knee from different angles in order to promote a better evaluation. The photos and videos were taken with an iPhone 6s Plus (Apple Inc., 1 Infinity Loop, Cupertino, California) using 12 Megapixel resolution for photos and 4 K at 30 fps resolution for videos.

The images were evaluated by three different observers who were blinded to the specimens' groups. Each observer was asked to score the images by using a central electronic database. In addition, the observers were asked to judge the quality of the information the images and videos provided of each knee. The quality of imaging information was assessed as poor quality (0 points), moderate quality (1 point) or good quality (2 points). The overall quality of the images was the sum of the judgment of all of the observers and was interpreted as follows: poor quality (0-2 points), moderate quality (3-4 points) or good quality (5-6 points). Each knee was scored according to the validated International Cartilage Repair Society (ICRS) macroscopic score system for cartilage repair ranging from 0 to 12 points (van den Borne et al. 2007). Higher scores represent better quality repairs. The observers were all experienced knee specialized orthopaedic surgeons well versed in performing and evaluating cartilage repair techniques. One of the observers was the first author (CEF) and the other two were not involved with the study, except for ICRS macroscopic rating (Table 1).

Macroscopic evaluation included analysis of nylon suture integrity around the eight peripheral holes of the parylene scaffold and parylene folding or delamination.

2.5 Histology

Following image and video acquisition for macroscopic evaluation, the resected distal femur was submerged in paraformaldehyde 10% (Ricca Chemical Company, Arlington, Texas) for 72 h for tissue fixation. For decalcification, the tissue was submerged in Decalcifier II (Leica Biosystems, Nussloch, Germany) for 48 h. Decalcifier II was changed and the tissue submerged for another 48 h. Decalcifier II was changed again for a third time, and the tissue was submerged for 24 h. Following decalcification, the tissue was dehydrated with 70% alcohol (BDH-VWR Analytical, Muskegon, Michigan). The distal femur was split in half at the sagittal plane and the medial and lateral portions of the trochlear lesion were embedded in paraffin. Using a microtome, 5 μm thickness slices were made. The samples were stained with hematoxylin-eosin (HE) and safranin-O.

Each femur was evaluated using a medial portion and a lateral portion of the lesion for a total of two slides per femur. Four different observers blinded to the specimens' group evaluated the samples. All observers had cartilage histology analysis experience prior to this study. Two observers participated as authors (CEF, BH) and two other observers were independent pathologists. Each slide from the six, nine and twelve weeks postoperatively time points, was scored using the safranin 0 staining according to the validated Pineda Scale, the histological score system for cartilage repair ranging from 0 to 13 points (Pineda et al. 1992; Rutgers et al. 2010). The Pineda scale was modified to incorporate inflammation in order to evaluate any parylene inflammatory reaction, modifying the score range to 0-15 points, and using HE staining to complement safranin 0 staining information. Lower scores represent better repair tissue quality. The three weeks postoperative samples were analyzed only for inflammation and parylene interaction to the host tissue (Table 2).

2.6 Immunostaining

The paraffin embedded tissue sections were processed for type II collagen immunofluorescent staining. Sections were first incubated with the mouse collagen II antibody at a dilution of 1:50 (Abcam, Cambridge, Massachusetts) overnight at 4° C. and then stained with the secondary antibody Alexa Fluor® 488 goat anti-mouse at a dilution of 1:650 (Abcam, Cambridge, Massachusetts) for 1 h followed by counter staining of nuclei with DAPI. Images were taken using the EVOS fluorescence microscope (Life Technologies, Gaithersburg, MD) for analysis.

2.7 Statistical Analysis

All data was analyzed using Prism? for Mac OS X (GraphPad Software, La Jolla, California). The Wilcoxon matched-pairs signed rank test was used to compare the parylene implanted knee to the contra-lateral knee of the same animal at the different post-operative time points groups. P values<0.05 were considered significant.

3 Results

Quantitative variables were expressed as mean±standard deviation.

3.1 Macroscopic Evaluation

Figures 4A, 4B, 4C, 4D:
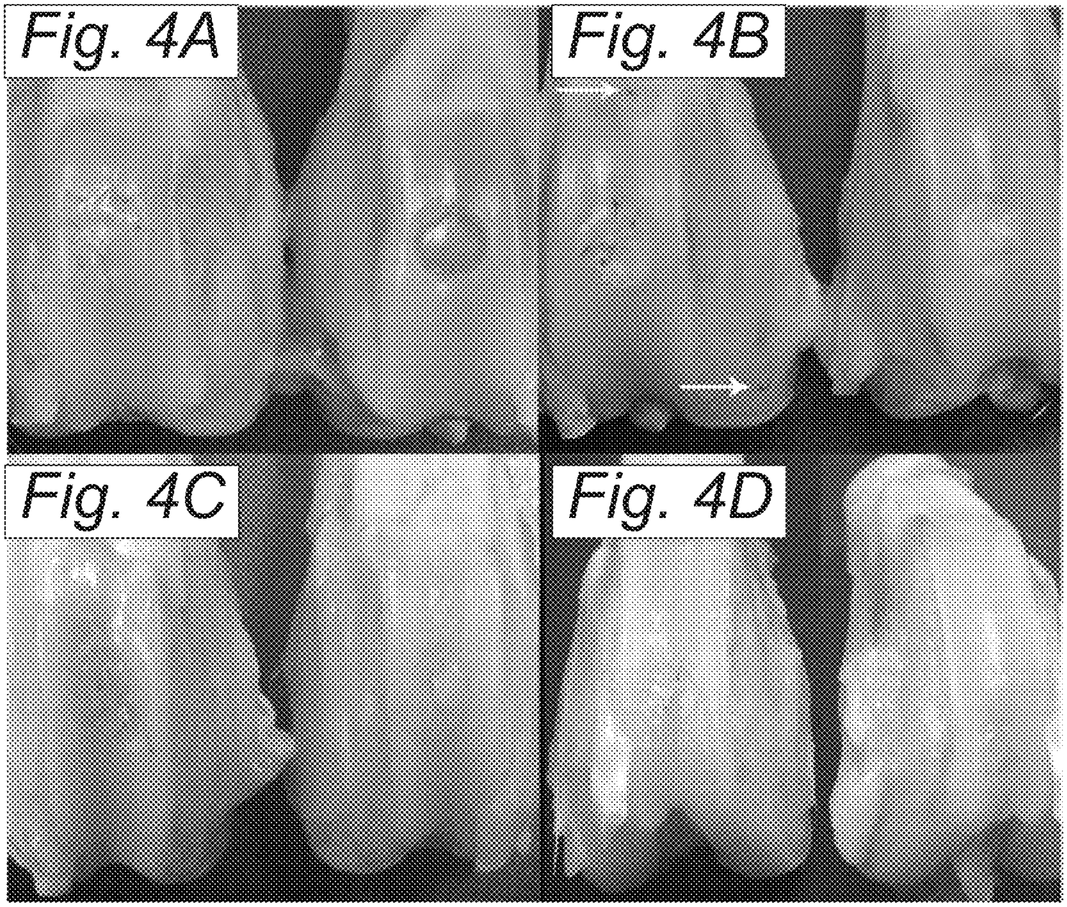
FIGS. 4A, 4B, 4C, and 4D: Macroscopic view of the parylene scaffold implanted in the right knee (depicted on the left in each photograph A-D) and its matched pair control left knee (depicted on the right in each photograph A-D) of 4 different animals A-D. A. Three week postoperative specimen demonstrating that the parylene implanted knee has one Nylon suture missing at the 4:30 o'clock position, with resultant parylene folding at the site of the missing suture. The parylene-implanted knee has a higher degree of defect repair level with the surrounding cartilage, better integration at the border zone and better macroscopic appearance than the control knee. B. Six week postoperative specimen, demonstrating that the parylene-implanted knee has a centripetal distribution of the sutures from 3:00 to 7:30 o'clock, showing folding at the site of the displaced and missing sutures, and demonstrating two broken sutures out of the cartilage zone (arrows). The parylene-implanted knee has a higher degree of defect repair level with the surrounding cartilage, higher integration with the border zone and better macroscopic appearance than the control knee which shows a large fissure/defect from 4 to 7 o'clock. C. Nine week postoperative explant, with the parylene implanted knee showing a centripetal distribution of the three remaining sutures from 4:30 to 7:30 o'clock, showing folding of the parylene, with the parylene-implanted knee demonstrating a higher degree of defect repair level with the surrounding cartilage, better integration with the border zone and better macroscopic appearance than the control knee which demonstrates a very large fissure at its center. D. Twelve week postoperative explant, with the parylene-implanted knee demonstrating a centripetal distribution of the two remaining sutures, demonstrating folding of the parylene, a higher degree of defect repair level with the surrounding cartilage, better integration with the border zone and better macroscopic appearance than the control knee which has a very large fissure/defect at its center and at its periphery
Figure 5A:
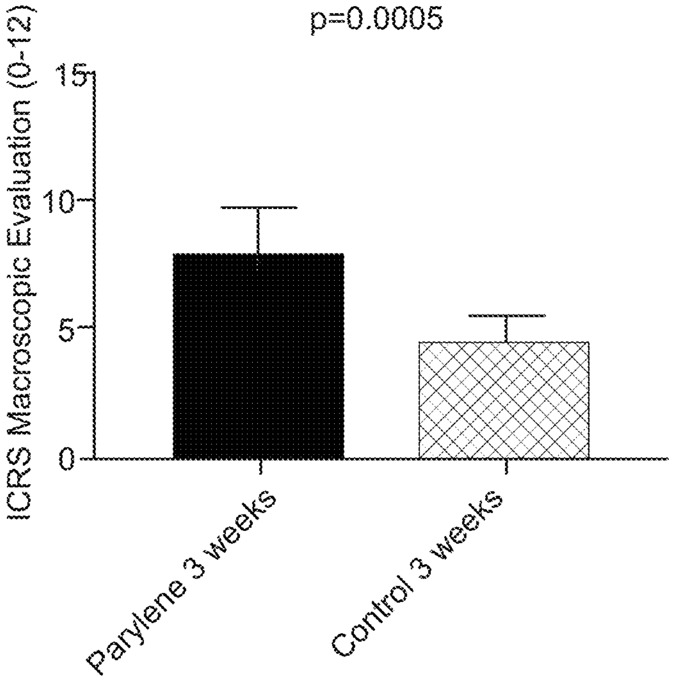
FIGS. 5A, 5B, 5C, and 5D: ICRS macroscopic score system for cartilage repair showing the mean±SD scores for each time point postoperatively. A. Three weeks postoperatively. B. Six weeks postoperatively. C. Nine weeks postoperatively. D. Twelve weeks postoperatively
Figure 5B:
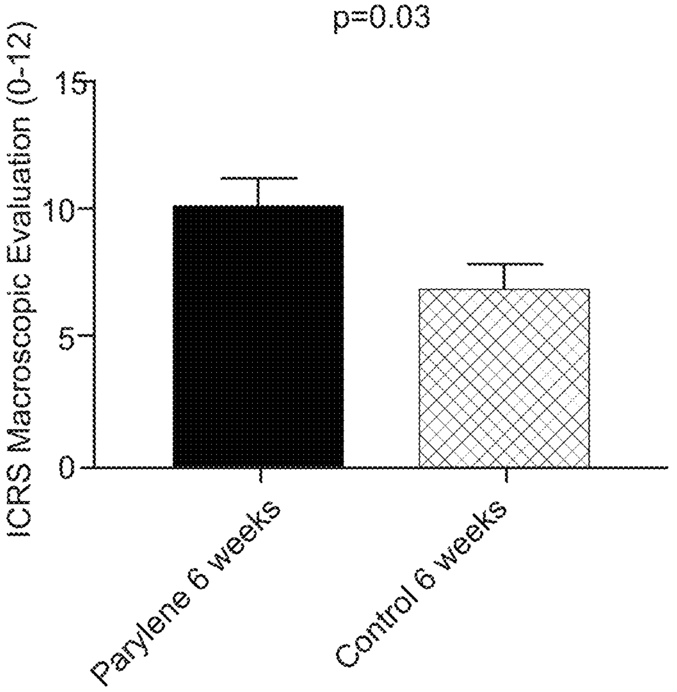
Figure 5C:
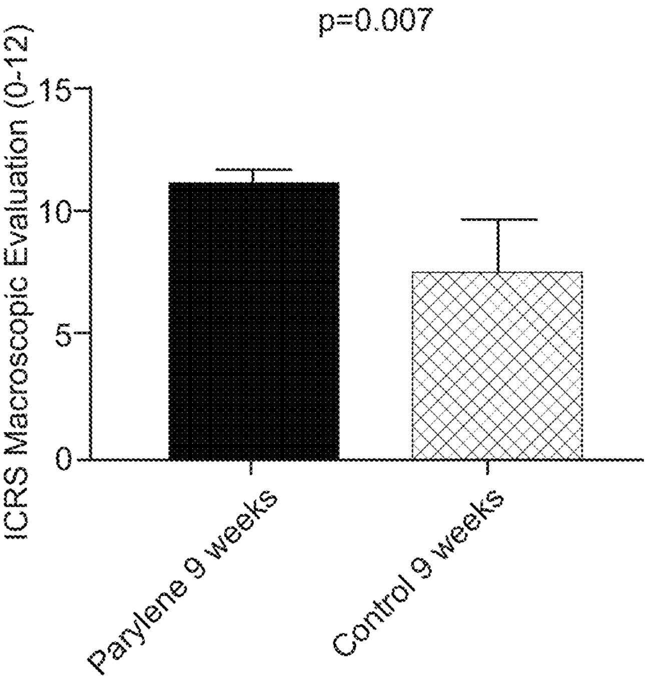
Figure 5D:
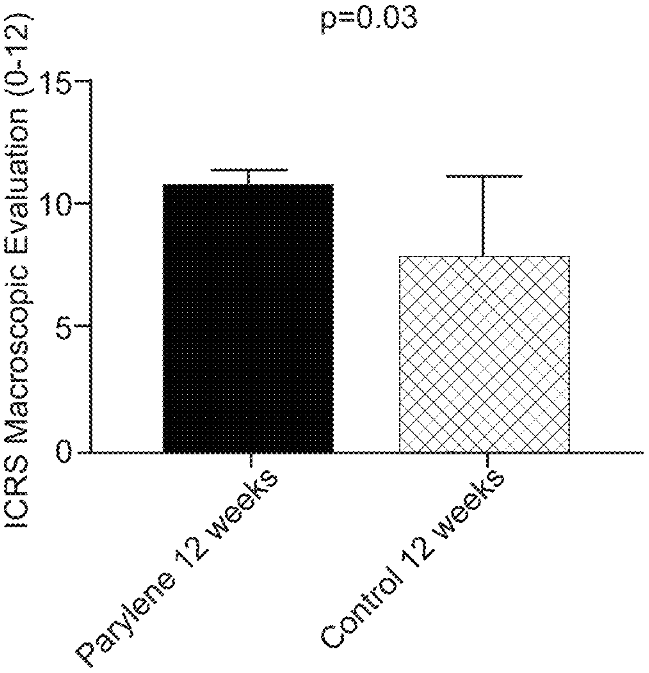
Figure 6A:
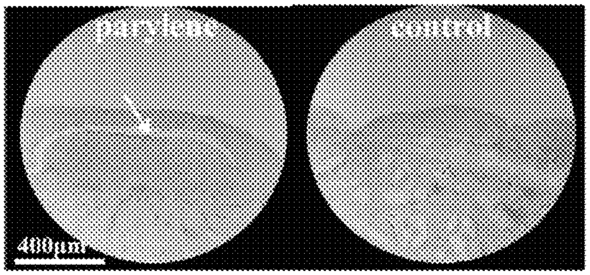
FIGS. 6A, 6B, 6C, 6D, 6E, and 6F: Example histological assessment with Safranin O staining of the parylene-implanted knee (depicted on the left in each image A-F) and its matched pair control knee (depicted on the right in each image A-F) of the same animal. The left column micrographs were taken at 4× magnification and the right column micrographs were taken at 40× magnification. A. Six week postoperative specimen, with the parylene implanted knee demonstrating better defect filling, better reconstruction of the osteochondral junction and better matrix staining (arrow represents the parylene scaffold engulfed inside the repair tissue). B. Six week postoperative specimen, with the parylene-implanted knee demonstrating better cell morphology (arrow represents the parylene scaffold engulfed inside the repair tissue). C. Nine week postoperative specimen, with the parylene-implanted knee demonstrating better reconstruction of the osteochondral junction and better matrix staining. D. Nine week postoperative specimen, with the parylene-implanted knee demonstrating better cell morphology. E. Twelve week postoperative specimen, with parylene-implanted knee demonstrating better reconstruction of the osteochondral junction and better matrix staining. F. Twelve week postoperative specimen, with the parylene-implanted knee presenting better cell morphology
Figure 6B:
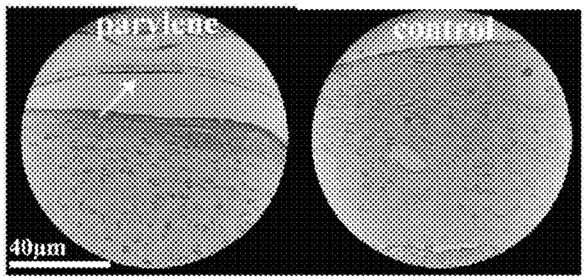
Figure 6C:
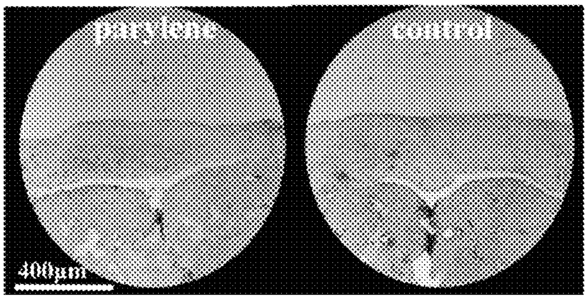
Figure 6D:
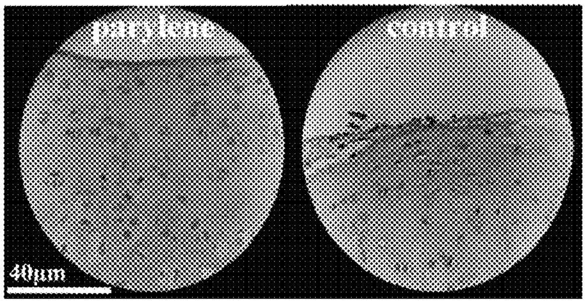
Figure 6E:
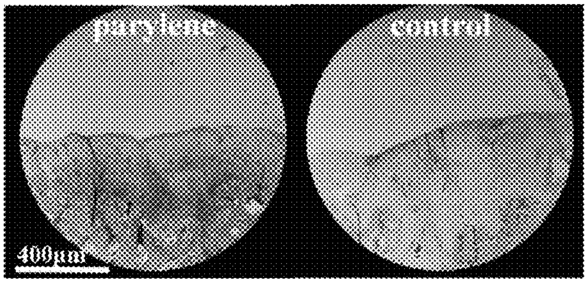
Figure 6F:
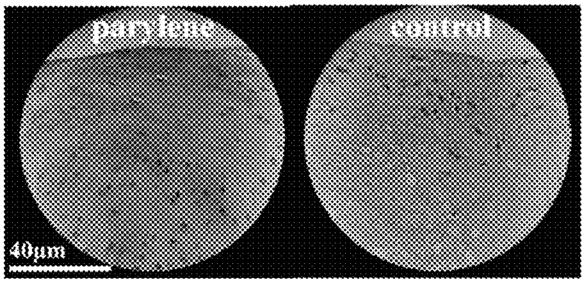

The quality of imaging information was rated as good quality for all knee specimens by all observers. The mean score was 5.59±0.49. Generally, parylene was visualized on the top of the repair tissue and demonstrated some level of folding or delamination. Nylon sutures were not always present, however, when they were, they were located at the insertion site or displaced with a centripetal distribution. Overall, parylene implanted knees demonstrated a higher degree of defect repair, better integration at the border zone, and better macroscopic appearance (FIG. 4). Parylene implanted knees achieved higher ICRS macroscopic scores for each evaluation group (FIG. 5).

3.2 Histology

Figure 7A:
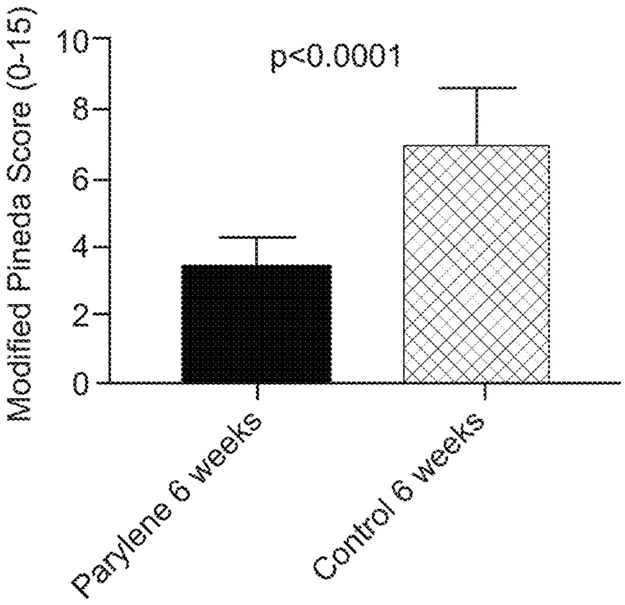
FIGS. 7A, 7B, and 7C: Histological score system for cartilage repair. Modified Pineda scale showing the mean±SD scores for each time point postoperatively analysis. A. Six weeks postoperatively. B. Nine weeks postoperatively. C. Twelve weeks postoperatively
Figure 7B:
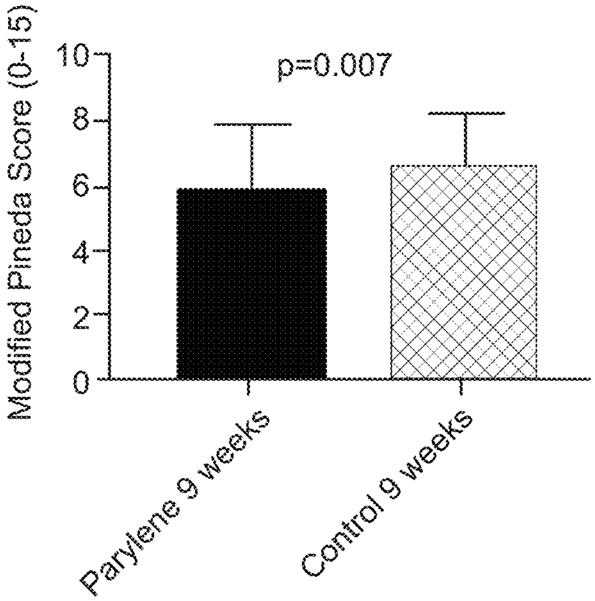
Figure 7C:
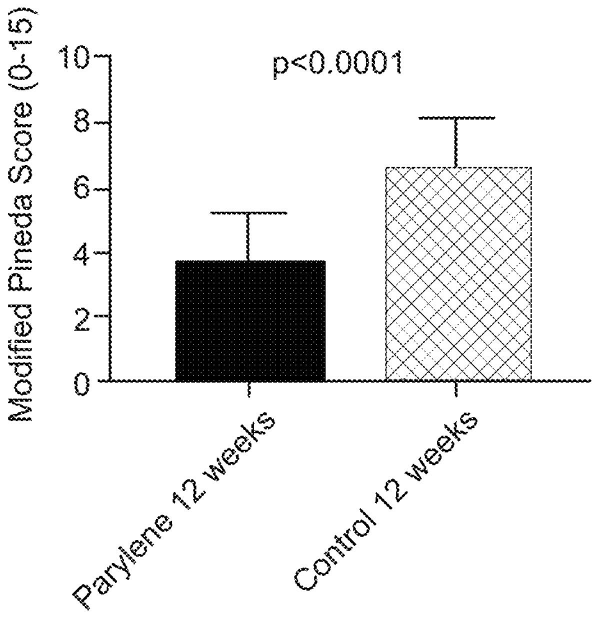

Filling of the defect, reconstruction of the osteochondral junction evaluated using Safranin O staining of the hyaline cartilage and matrix staining were generally evaluated using 4× microscope magnification. Cell morphology was usually evaluated using 40× microscope magnification. Overall, parylene-implanted knees demonstrated better defect filling, better reconstruction of the osteochondral junction, better matrix staining and better cell morphology (FIG. 6). As such, parylene implanted knees achieved lower modified Pineda scores at each time point (FIG. 7).

Figure 8A:
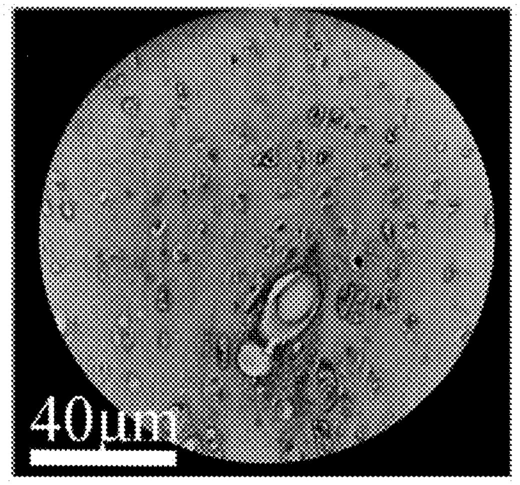
FIGS. 8A, 8B, and 8C: Histological assessment with Safranin O staining. A and B. 40× magnification micrographs showing encapsulated nylon debris. C. 20× magnification micrograph showing parylene engulfed inside the repair tissue and some nylon debris
Figure 8B:
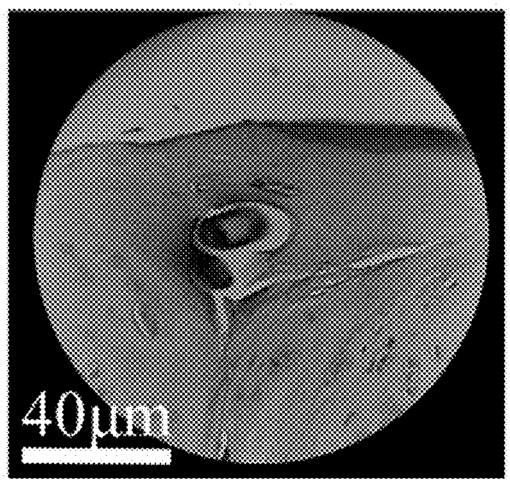
Figure 8C:
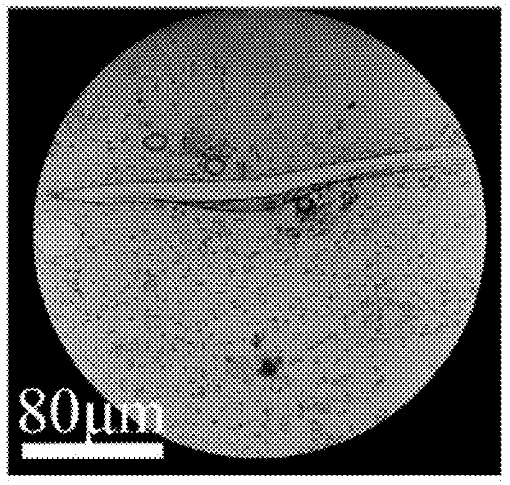

No parylene-implanted specimen demonstrated an inflammatory reaction at any time point. Nylon debris were visualized in some parylene-implanted knees (FIG. 8). Parylene was seen in just 20% of the prepared histological slides and it was always engulfed inside the repair tissue (FIG. 8), likely due to delamination at the time of fixation.

Figure 9A:
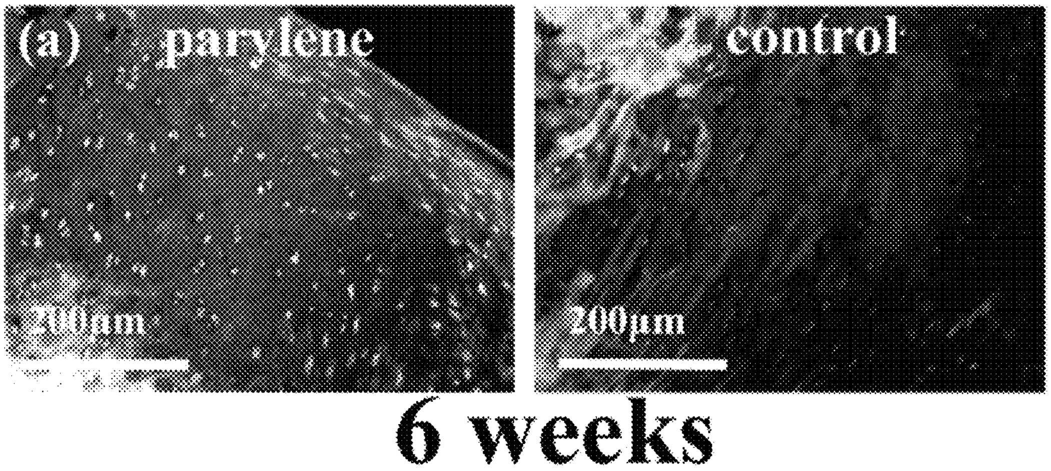
FIGS. 9A, 9B, and 9C: Collagen II immunostaining (green in the original photograph) of the parylene scaffold implanted knee and its matched pair control knee at different time points. Micrographs were taken using 8× magnification. A. Six weeks postoperatively, the parylene implanted knee demonstrated higher collagen II expression. B. Nine weeks postoperatively, the parylene implanted knee presented slightly higher collagen II expression. C. Twelve weeks postoperatively, the parylene implanted knee demonstrated higher collagen II expression
Figure 9B:
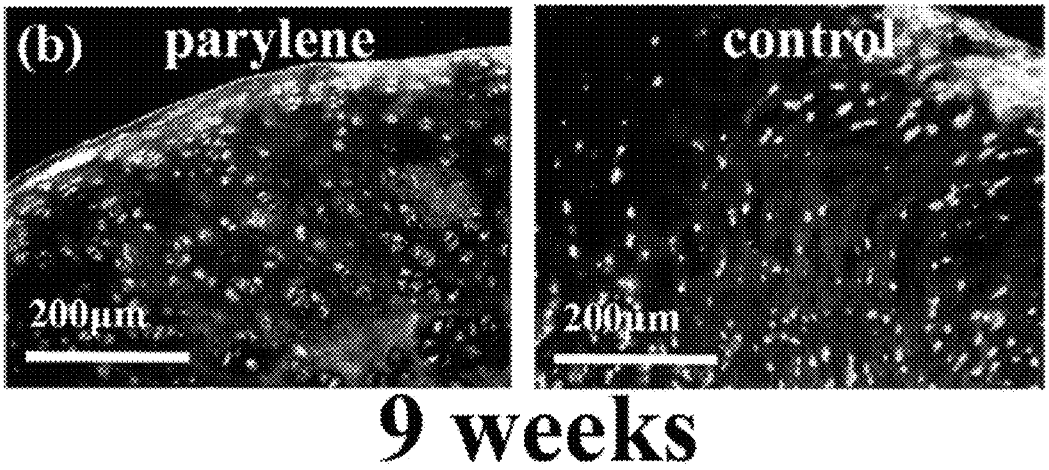
Figure 9C:
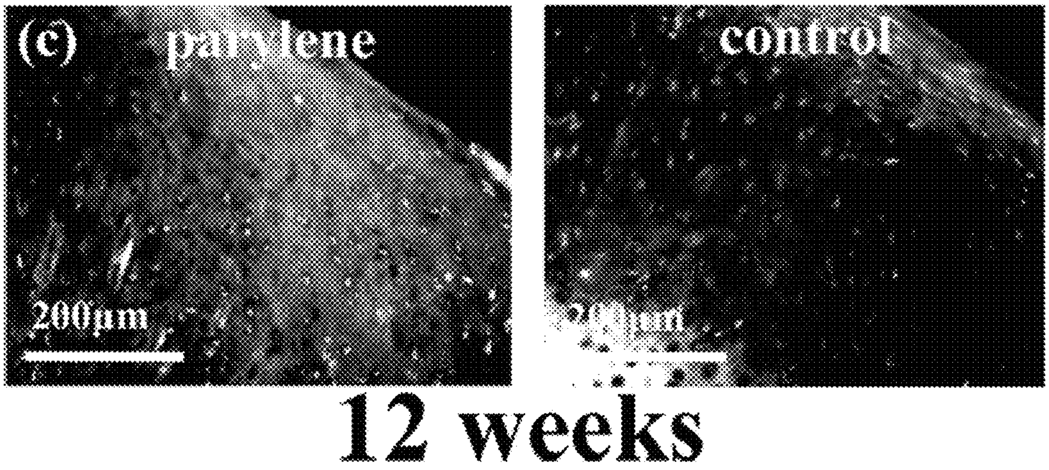

Parylene implanted knees demonstrated higher collagen II expression via immunostaining in comparison to the control knees (FIG. 9).

4 Discussion

The most important finding of this study was that the parylene implanted knees demonstrated significantly better repair characteristics than control knees. This superiority was consistent across all time-points evaluated, both macroscopically and microscopically. This finding was rendered more robust by our matched pair comparison methodology, which eliminated confounding factors such as individual healing disparities. These results show that the parylene scaffold can treat cartilage lesions by introducing a combination of a reparative and a superficial reconstructive procedure. The reparative procedure was represented by the microfracture bone marrow stimulating technique, and the superficial reconstructive procedure was represented by the parylene scaffold acting as a protective cap, shielding the underlying repair tissue. Although a similar approach was proposed by the AMIC procedure, augmenting the microfracture technique with an absorbable three-dimensional scaffold leading to better results than microfracture alone, our use of a nonabsorbable superficial scaffold is a new approach showing promising results and potential for future applications (Anders et al. 2013; Gracitelli et al. 2016).

The use of a non-absorbable scaffold to augment the reparative procedure demonstrates superiority to the reparative procedure alone as well as the more traditional approach using bioabsorbable scaffolds. In addition, since the parylene scaffold can be seeded with cells and manufactured to allow nutrients and macromolecules diffusion through the use of micropores, it can also be used as a regenerative cell based therapy for cartilage lesions using either autologous chondrocytes or stem cells. It can potentially replace periosteal flaps and bioabsorbable membranes used for autologous chondrocytes implantation and scaffold based stem cell therapies. This expands the applications of the non-absorbable scaffold as a protective membrane overlying the repair tissue. (Anders et al. 2013; Christensen et al. 2012; Diniz et al. 2013; Gracitelli et al. 2016; Levingstone et al. 2016; Lu et al. 2012; O'Conor et al. 2013; Peterson et al. 2000; Poole et al. 2001).

Since this was the first study to evaluate this biomedical microdevice in the treatment of cartilage lesions, it is important to note that rabbit cartilage repair tissue reaches maturity approximately 12 weeks postoperatively so this is one of the most used time points to evaluate cartilage lesion treatments in a rabbit model. Since we intended to analyze also the earlier phases of the repair tissue and parylene influence over its maturation and possible inflammation, this study also included earlier time point analyses (Christensen et al. 2012; Levingstone et al. 2016; Rutgers et al. 2010).

Parylene-implanted knees demonstrated better matrix staining in comparison to the control knees according to the Pineda classification. The sections were stained with Safranin O, with hyaline cartilage normally staining red. Lack of matrix coloration, represented by the blue color found in cationic stains such as Safranin O can be indicative of long-standing cartilage matrix proteoglycan depletion. The red matrix staining is related to a more normal proteoglycan content in the parylene-implanted knees. Also, parylene implanted knees expressed higher amounts of collagen II in comparison to the control knees. This is the most important collagen compound in cartilage and its higher expression is related to a more chondrogenic matrix and better repair tissue quality. Since the 9 μm thick parylene C scaffold has a very low permeability for gases, including oxygen, except at the eight peripheral 200 μm holes intended for suture passage, hypoxia could explain why the repair tissue consisted of more cartilage than fibrocartilage. Hypoxia enhances chondrogenic potential of mesenchymal stem cells (Adesida et al. 2012; Anderson et al. 2016; Portron et al. 2015). Since the cartilage lesion model used in this study acted not only as a lesion but also, through subchondral bone bleeding, as a bone marrow stimulation reparative technique similar to microfracture, the healing response was mainly mediated by the bone marrow mesenchymal stem cells that migrated into the blood clot. The parylene scaffold likely created a more hypoxic environment, optimizing the bone marrow derived mesenchymal stem cells' chondrogenic potential. This can be an explanation for the better histological Pineda scores at all time points for the parylene scaffold in comparison to the controls. Another potential reason for the better scores would be the mechanical advantage and protection conferred by the parylene scaffold to the repair tissue during healing maturation process. This has the advantage of increasing the stiffness of the complex, helping it withstand patellofemoral shear forces, and possibly optimizing mechanotransduction signals over the restorative cells and inducing a better differentiation of the bone marrow derived mesenchymal stem cells toward cartilage (Franciozi et al. 2013; Mankin 1982; O'Conor et al. 2013).

Macroscopic evaluation correlated well with the histological analysis in that parylene-implanted knees achieved better scores at all time points than control knees using both rating systems. Defect filling and reconstruction of the osteochondral junction or integration to the border zone can be highly rated using a histological slide. However, it may represent just a portion, missing the general tissue response seen on macroscopic evaluation, demonstrating the importance of utilizing both analysis techniques to determine the efficacy of such repair strategies. In these cases, increasing the number of histologic sections can also mitigate the disparity, justifying the evaluation of the medial and lateral side of each cartilage lesion at this study (Mainil-Varlet et al. 2010; Mankin 1982; Mooj en et al. 2002; O'Driscoll et al. 1986; Peterson et al. 2000; Pineda et al. 1992; Rutgers et al. 2010; Smith et al. 2005; van den Borne et al. 2007).

Nylon sutures were not always present after explanation. They may have broken because of patellofemoral shear forces during range of motion excursions of the knees or they could have broken during repair tissue ingrowth. When they were present, they were located at their implantation site or demonstrated a centripetal distribution. The centripetal distribution may have been caused by patellofemoral shear forces, which broke the nylon sutures and displaced them with the folded and delaminated parylene scaffold through centripetal repair tissue ingrowth. Partially folded and delaminated parylene was always found combined with broken nylon sutures suggesting that the parylene scaffold could withstand the patellofemoral shear forces as long as its suture fixation was intact. Despite the evaluation of different time points, it was not possible to define a time dependent suture survivorship analysis due to data heterogeneity.

No inflammatory response was seen in the parylene implanted knees at any time point using the modified Pineda score substantiating its use for cartilage lesion treatment. However, some 10-0 nylon debris was found around the repair tissue, usually encapsulated. This most likely was a result of the suture breakage (Pineda et al. 1992; Rutgers et al. 2010).

As parylene was seen in just 20% of the prepared histological slides and was always engulfed inside the repair tissue, it probably sheared off during sample sectioning when it was located at the top of the tissue. This is supported by the fact that the parylene scaffolds visualized on the top were partially delaminated before undergoing the histological preparation, so chances are that with less structural support from the sutures they broke off from the sample, given that most slices did not contain any sutures at all. Of note, none of the parylene seen at the top of the repairs on macroscopic specimens was visualized after histological preparation. Since parylene's melting point is 290° C., it would not melt during paraffin infiltration at 60° C.

5. Limitations

No ELISA, RNA extraction, polymerase chain reaction gene expression or more complex analyses were made. However, the experiments set forth herein are sufficient to demonstrate parylene scaffold feasibility in the treatment of cartilage lesions. The study included three six weeks animals. One animal was needed to refine anesthesia, surgical approach, and histologic procedures and these data were not included in our results. Four animals were used for each of the remaining time point groups to strengthen our outcomes. The three week postoperatively animals were not evaluated using the modified Pineda histological classification. Instead, they were just analyzed for the presence of inflammation, suture breakage, parylene folding or delamination and parylene interaction with the host tissue.

6. Conclusion

Parylene scaffolds are a feasible option for cartilage lesion treatment and the combination of a reparative to a superficial reconstructive procedure using parylene scaffolds led to better results than the reparative procedure alone.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

A. B. Adesida, A. Mulet-Sierra, N. M. Jomha, Hypoxia mediated isolation and expansion enhances the chondrogenic capacity of bone marrow mesenchymal stromal cells. Stem Cell Res Ther 3, 9 (2012)

S. Anders, M. Volz, H. Frick, J. Gellissen, A randomized, controlled trial comparing autologous matrix-induced Chondrogenesis (AMIC®) to Microfracture: Analysis of 1- and 2-year follow-up data of 2 centers. Open Orthop J 7, 133-143 (2013)

D. E. Anderson, B. D. Markway, D. Bond, H. E. McCarthy, B. Johnstone, Responses to altered oxygen tension are distinct between human stem cells of high and low chondrogenic capacity. Stem Cell Res Ther 7, 154 (2016)

B. B. Christensen, C. B. Foldager, O. M. Hansen, A. A. Kristiansen, D. Q. Le, A. D. Nielsen, J. V. Nygaard, C. E. Bunger, M. Lind, A novel nano-structured porous polycaprolactone scaffold improves hyaline cartilage repair in a rabbit model compared to a collagen type I/III scaffold: In vitro and in vivo studies. Knee Surg. Sports Traumatol. Arthrosc. 20, 1192-1204 (2012)

C. R. Chu, M. Szczodry, S. Bruno, Animal models for cartilage regeneration and repair. Tissue Eng Part B Rev 16, 105-115 (2010)

F. Cicuttini, C. Ding, A. Wluka, S. Davis, P. R. Ebeling, G. Jones, Association of cartilage defects with loss of knee cartilage in healthy, middle-age adults: A prospective study. Arthritis Rheum. 52, 2033-2039 (2005)

C. Ding, F. Cicuttini, F. Scott, H. Cooley, C. Boon, G. Jones, Natural history of knee cartilage defects and factors affecting change. Arch. Intern. Med. 166, 651-658 (2006)

B. Diniz, P. Thomas, B. Thomas, R. Ribeiro, Y. Hu, R. Brant, A. Ahuja, D. Zhu, L.

Liu, M. Koss, M. Maia, G. Chader, D. R. Hinton, M. S. Humayun, Subretinal implantation of retinal pigment epithelial cells derived from human embryonic stem cells: Improved survival when implanted as a monolayer. Invest. Ophthalmol. Vis. Sci. 54, 5087-5096 (2013)

C. E. Franciozi, V. A. Tarini, R. D. Reginato, P. R. Goncalves, V. P. Medeiros, M. Ferretti, J. L. Dreyfuss, H. B. Nader, F. Faloppa, Gradual strenuous running regimen predisposes to osteoarthritis due to cartilage cell death and altered levels of glycosaminoglycans. Osteoarthr. Cartil. 21, 965-972 (2013)

G. C. Gracitelli, V. Y. Moraes, C. E. Franciozi, M. V. Luzo, J. C. Belloti, Surgical interventions (microfracture, drilling, mosaicplasty, and allograft transplantation) for treating isolated cartilage defects of the knee in adults. Cochrane Database Syst. Rev. 9, CD010675 (2016)

E. B. Hunziker, L. C. Rosenberg, Repair of partial-thickness defects in articular cartilage: Cell recruitment from the synovial membrane. J. Bone Joint Surg. Am. 78, 721-733 (1996)

T. J. Levingstone, E. Thompson, A. Matsiko, A. Schepens, J. P. Gleeson, F. J. O'Brien, Multi-layered collagen-based scaffolds for osteochondral defect repair in rabbits. Acta Biomater. 32, 149-160 (2016)

M. Lind, F. Menhert, A. B. Pedersen, The first results from the Danish ACL reconstruction registry: Epidemiologic and 2 year follow-up results from 5,818 knee ligament reconstructions. Knee Surg. Sports Traumatol. Arthrosc. 17, 117-124 (2009)

B. Lu, D. Zhu, D. Hinton, M. S. Humayun, Y. C. Tai, Mesh-supported submicron parylene-C membranes for culturing retinal pigment epithelial cells. Biomed. Microdevices 14, 659-667 (2012)

P. Mainil-Varlet, B. Van Damme, D. Nesic, G. Knutsen, R. Kandel, S. Roberts, A new histology scoring system for the assessment of the quality of human cartilage repair: ICRS II. Am. J. Sports Med. 38, 880-890 (2010)

H. J. Mankin, The response of articular cartilage to mechanical injury. J. Bone Joint Surg. Am. 64, 460-466 (1982)

V. M. Mattila, R. Sihvonen, J. Paloneva, L. Fellander-Tsai, Changes in rates of arthroscopy due to degenerative knee disease and traumatic meniscal tears in Finland and Sweden. Acta Orthop. 87, 5-11 (2016)

D. J. Mooj en, D. B. Saris, K. G. Auw Yang, W. J. Dhert, A. J. Verbout, The correlation and reproducibility of histological scoring systems in cartilage repair. Tissue Eng. 8, 627-634 (2002)

C. J. O'Conor, N. Case, F. Guilak, Mechanical regulation of chondrogenesis. Stem Cell Res Ther 4, 61 (2013)

S. W. O'Driscoll, F. W. Keeley, R. B. Salter, The chondrogenic potential of free autogenous periosteal grafts for biological resurfacing of major full-thickness defects in joint surfaces under the influence of continuous passive motion. An experimental investigation in the rabbit. J. Bone Joint Surg. Am. 68, 1017-1035 (1986)

L. Peterson, T. Minas, M. Brittberg, A. Nilsson, E. Sjogren-Jansson, A. Lindahl, Two- to 9-year outcome after autologous chondrocyte transplantation of the knee. Clin. Orthop. Relat. Res., 212-234 (2000)

S. Pineda, A. Pollack, S. Stevenson, V. Goldberg, A. Caplan, A semiquantitative scale for histologic grading of articular cartilage repair. Acta Anat. (Basel) 143, 335-340 (1992)

A. R. Poole, T. Kojima, T. Yasuda, F. Mwale, M. Kobayashi, S. Laverty, Composition and structure of articular cartilage: A template for tissue repair. Clin. Orthop. Relat. Res., S26-S33 (2001)

S. Portron, V. Hivernaud, C. Merceron, J. Lesoeur, M. Masson, O. Gauthier, C. Vinatier, L. Beck, J. Guicheux, Inverse regulation of early and late chondrogenic differentiation by oxygen tension provides cues for stem cell-based cartilage tissue engineering. Cell. Physiol. Biochem. 35, 841-857 (2015)

B. Pouran, V. Arbabi, A. A. Zadpoor, H. Weinans, Isolated effects of external bath osmolality, solute concentration, and electrical charge on solute transport across articular cartilage. Med. Eng. Phys. 38, 1399-1407 (2016)

D. C. Rodger, A. J. Fong, W. Li, H. Ameri, A. K. Ahuj a, C. Gutierrez, I. Lavrov, H. Zhong, P. R. Menon, E. Meng, J. W. Burdick, R. R. Roy, V. Reggie Edgerton, J. D. Weiland, M. S. Humayun, Y.-C. Tai, Flexible parylene-based multielectrode array technology for highdensity neural stimulation and recording. Sensors Actuators B Chem. 132, 449-460 (2008)

M. Rutgers, M. J. van Pelt, W. J. Dhert, L. B. Creemers, D. B. Saris, Evaluation of histological scoring systems for tissue-engineered, repaired and osteoarthritic cartilage. Osteoarthr. Cartil. 18, 12-23 (2010)

F. Shapiro, S. Koide, M. J. Glimcher, Cell origin and differentiation in the repair of full-thickness defects of articular cartilage. J. Bone Joint Surg. Am. 75, 532-553 (1993)

G. D. Smith, J. Taylor, K. F. Almqvist, C. Erggelet, G. Knutsen, M. Garcia Portabella, T. Smith, J. B. Richardson, Arthroscopic assessment of cartilage repair: A validation study of 2 scoring systems. Arthroscopy 21, 1462-1467 (2005)

M. P. van den Borne, N. J. Raijmakers, J. Vanlauwe, J. Victor, S. N. de Jong, J. Bellemans, D. B. Saris, Society International Cartilage Repair, International cartilage repair Society (ICRS) and Oswestry macroscopic cartilage evaluation scores validated for use in autologous chondrocyte implantation (ACI) and microfracture. Osteoarthr. Cartil. 15, 1397-1402 (2007)

W. Widuchowski, J. Widuchowski, T. Trzaska, Articular cartilage defects: Study of 25, 124 knee arthroscopies. Knee 14, 177-182 (2007)

Zumstein, M. A., et al. "The Biology of Rotator Cuff Healing." Orthopaedics & Traumatology: Surgery & Research, vol. 103, no. 1, 2017, doi:10.1016/j.otsr.2016.11.003.

Hernigou, Philippe, et al. "Biologic Augmentation of Rotator Cuff Repair with Mesenchymal Stem Cells during Arthroscopy Improves Healing and Prevents Further Tears: a Case-Controlled Study." International Orthopaedics, vol. 38, no. 9, 2014, pp. 1811-1818., doi:10.1007/s00264-014-2391-1.

Schlegel, Theodore F., et al. "Radiologic and Clinical Evaluation of a Bioabsorbable Collagen Implant to Treat Partial-Thickness Tears: a Prospective Multicenter Study." Journal of Shoulder and Elbow Surgery, vol. 27, no. 2, 2018, pp. 242-251., doi:10.1016/j.jse.2017.08.023.

Lederman, Evan S., et al. "A Prospective, Multicenter Study to Evaluate Clinical and Radiographic Outcomes in Primary Rotator Cuff Repair Reinforced with a Xenograft Dermal Matrix." Journal of Shoulder and Elbow Surgery, vol. 25, no. 12, 2016, pp. 1961-1970., doi:10.1016/j jse.2016.02.029.

Gillespie, Robert J., et al. "Biologic and Synthetic Grafts in the Reconstruction of Large to Massive Rotator Cuff Tears." Journal of the American Academy of Orthopaedic Surgeons, vol. 24, no. 12, 2016, pp. 823-828., doi: 10.5435/jaaos-d-15-00229.

Yoon, Jong Pil, et al. "Outcomes of Combined Bone Marrow Stimulation and Patch Augmentation for Massive Rotator Cuff Tears." The American Journal of Sports Medicine, vol. 44, no. 4, 2016, pp. 963-971., doi:10.1177/0363546515625044.

Gomes, Joao L. Ellera, et al. "Conventional Rotator Cuff Repair Complemented by the Aid of Mononuclear Autologous Stem Cells." Knee Surgery, Sports Traumatology, Arthroscopy, vol. 20, no. 2, 2011, pp. 373-377., doi:10.1007/s00167-011-1607-9.

Mazzocca, Augustus D., et al. "Rapid Isolation of Human Stem Cells (Connective Tissue Progenitor Cells) From the Proximal Humerus During Arthroscopic Rotator Cuff Surgery." The American Journal of Sports Medicine, vol. 38, no. 7, 2010, pp. 1438-1447., doi: 10.1177/0363546509360924.

Mazzocca, Augustus D., et al. "Bone Marrow-Derived Mesenchymal Stem Cells Obtained During Arthroscopic Rotator Cuff Repair Surgery Show Potential for Tendon Cell Differentiation After Treatment With Insulin." Arthroscopy: The Journal of Arthroscopic & Related Surgery, vol. 27, no. 11, 2011, pp. 1459-1471., doi: 10.1016/j.arthro.2011.06.029.

"REGENETEN?." REGENETEN Rotator Cuff Bioinductive Implant for Rotator Cuff Repair|Smith & Nephew—US Professional, 2019, www.smith-nephew.com/professional/products/all-products/regeneten-/.

Proctor, Christopher S. "Long-Term Successful Arthroscopic Repair of Large and Massive Rotator Cuff Tears with a Functional and Degradable Reinforcement Device." Journal of Shoulder and Elbow Surgery, vol. 23, no. 10, 2014, pp. 1508-1513., doi:10.1016/j.jse.2014.01.010.

What is claimed is:

1. A polymeric scaffold apparatus for articular cartilage regeneration, the apparatus comprising:

a non-absorbable parylene sheet having suture holes around a periphery of the sheet that surrounds a central portion of the sheet, wherein the parylene sheet has been produced by lithographically etching a parylene layer to a predetermined shape; and wherein the parylene sheet consists of parylene C, parylene D, parylene N, parylene HT, parylene A, or parylene AM, and optionally mesenchymal stem cells, autologous chondrocytes, or a biological factor.

2. The apparatus of claim 1 wherein the sheet is parylene C and is at least 9 μm thick.

3. The apparatus of claim 2 wherein the sheet is between 100 μm and 1000 μm thick.

4. The apparatus of claim 1 wherein the sheet has at least 8 suture holes around the periphery.

5. The apparatus of claim 1, wherein the mesenchymal stem cells are embedded in or adsorbed on the sheet.

6. The apparatus of claim 5 wherein the mesenchymal stem cells are derived from bone marrow.

7. The apparatus of claim 1, further comprising:

wherein the autologous chondrocytes are embedded in or adsorbed on the sheet.

8. The apparatus of claim 1, wherein the biological factor is embedded in or adsorbed on the sheet, the biological factor selected from the group consisting of a cell adhesion factor, a growth factor, and a cytokine.

9. The apparatus of claim 8 wherein the cell adhesion factor is selected from the group consisting of fibronectin, laminin, collagen, vitronectin, and tenascin.

10. The apparatus of claim 1, further comprising:

sutures in the suture holes configured to affix the sheet to a cartilage.

11. The apparatus of claim 10 wherein the sheet is configured to cover a chondral defect in the cartilage.

12. The apparatus of claim 11, wherein the sheet was etched to an area from 1 percent to 20 percent larger than the chondral defect.

13. The apparatus of claim 11 wherein the sheet is configured to cover a drill hole in subchondral bone that penetrates to bone marrow in the bone.

14. The apparatus of claim 13 wherein the sheet is configured to cover a blood clot caused by bleeding from the drill hole.

15. The apparatus of claim 1 wherein the sheet is engulfed inside repair tissue.

16. A polymeric scaffold apparatus for tendon repair or regeneration, the apparatus comprising:

a non-absorbable parylene sheet having:

a thickness between 100 μm and 1000 μm;

0.010 μm- to 5 μm-diameter micropores therein; and suture holes around a periphery of the sheet that surrounds a central portion of the sheet, wherein the parylene sheet has been produced by lithographically etching a parylene layer to a predetermined shape; and wherein the parylene sheet consists of parylene C, parylene D, parylene N, parylene HT, parylene A, or parylene AM, and optionally mesenchymal stem cells, autologous chondrocytes, or a biological factor.

17. The apparatus of claim 16 wherein the sheet has at least 8 suture holes around the periphery.

18. The apparatus of claim 16 wherein the mesenchymal stem cells are embedded in or adsorbed on the sheet.

19. The apparatus of claim 16 wherein the autologous chondrocytes are embedded in or adsorbed on the sheet.

20. The apparatus of claim 16 wherein the biological factor is embedded in or adsorbed on the sheet, the biological factor selected from the group consisting of a cell adhesion factor, a growth factor, and a cytokine.

21. The apparatus of claim 20 wherein the cell adhesion factor is selected from the group consisting of fibronectin, laminin, collagen, vitronectin, and tenascin.

22. The apparatus of claim 16, further comprising:

sutures in the suture holes configured to affix the sheet to a rotator tendon or a rotator cuff.

23. The apparatus of claim 22 wherein the sheet is configured to cover a defect in the rotator tendon or a tear in the rotator cuff.

24. The apparatus of claim 23, wherein the sheet was etched to an area from 1 percent to 20 percent larger than the defect in the rotator tendon or the tear in the rotator cuff.

25. The apparatus of claim 16 wherein the sheet is engulfed inside repair tissue.

* * * * *